(12) United States Patent
Kopelman et al.

(10) Patent No.: US 8,805,563 B2
(45) Date of Patent: *Aug. 12, 2014

(54) METHOD FOR MANIPULATING A DENTAL VIRTUAL MODEL, METHOD FOR CREATING PHYSICAL ENTITIES BASED ON A DENTAL VIRTUAL MODEL THUS MANIPULATED, AND DENTAL MODELS THUS CREATED

(71) Applicant: Cadent Ltd., Or Yehuda (IL)

(72) Inventors: Avi Kopelman, Palo Alto, CA (US); Eldad Taub, Reut (IL)

(73) Assignee: Cadent Ltd., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/716,008

(22) Filed: Dec. 14, 2012

(65) Prior Publication Data
US 2013/0204601 A1    Aug. 8, 2013

Related U.S. Application Data

(63) Continuation of application No. 13/227,435, filed on Sep. 7, 2011, now Pat. No. 8,359,115, which is a continuation of application No. 12/654,762, filed on Dec. 31, 2009, now Pat. No. 8,041,439, which is a continuation of application No. 12/222,287, filed on Aug. 6, 2008, now Pat. No. 7,734,368, which is a continuation of application No. 11/349,124, filed on Feb. 8, 2006, now Pat. No. 7,555,403.

(60) Provisional application No. 60/699,499, filed on Jul. 15, 2005.

(51) Int. Cl.
G06F 19/00     (2011.01)

(52) U.S. Cl.
USPC ............................................. 700/98; 382/154

(58) Field of Classification Search
USPC ..................... 700/98, 117–118; 382/154, 128; 433/24, 29, 213
See application file for complete search history.

(56) References Cited

U.S. PATENT DOCUMENTS

| | | | |
|---|---|---|---|
| 5,938,446 A | 8/1999 | Andersson et al. | |
| 6,099,314 A | 8/2000 | Kopelman et al. | |
| 6,174,168 B1 | 1/2001 | Dehoff et al. | |
| 6,488,503 B1 | 12/2002 | Lichkus et al. | |
| 6,594,539 B1 | 7/2003 | Geng | |
| 7,184,150 B2 * | 2/2007 | Quadling et al. | 356/602 |
| 7,555,403 B2 | 6/2009 | Kopelman et al. | |

(Continued)

FOREIGN PATENT DOCUMENTS

| | | |
|---|---|---|
| WO | WO 00/08415 A1 | 2/2000 |
| WO | WO 2004/030565 A1 | 4/2004 |
| WO | WO 2004/087000 A1 | 10/2004 |

*Primary Examiner* — Kidest Bahta
(74) *Attorney, Agent, or Firm* — Wilson Sonsini Goodrich & Rosati

(57) ABSTRACT

A 3D virtual model of an intra oral cavity in which at least a part of a finish line of a preparation is obscured is manipulated in virtual space by means of a computer or the like to create, recreate or reconstruct finish line data and other geometrical corresponding to the obscured part. Trimmed virtual models, and trimmed physical models, can then be created utilizing data thus created. The virtual models and/or the physical models may be used in the design and manufacture of copings or of prostheses.

20 Claims, 8 Drawing Sheets

(56) References Cited

U.S. PATENT DOCUMENTS

| | | |
|---|---|---|
| 7,698,068 B2 | 4/2010 | Babayoff |
| 7,734,368 B2 | 6/2010 | Kopelman et al. |
| 8,041,439 B2 | 10/2011 | Kopelman et al. |
| 8,359,115 B2 | 1/2013 | Kopelman et al. |
| 2002/0015934 A1 | 2/2002 | Rubbert et al. |
| 2002/0137011 A1 | 9/2002 | Shoher et al. |
| 2004/0158342 A1 | 8/2004 | Wolf et al. |
| 2005/0177266 A1 | 8/2005 | Kopelman et al. |
| 2005/0251281 A1 | 11/2005 | O'Brien et al. |
| 2005/0271996 A1 | 12/2005 | Sporbert et al. |
| 2005/0283065 A1 | 12/2005 | Babayoff |
| 2006/0001739 A1 | 1/2006 | Babayoff |
| 2006/0122719 A1 | 6/2006 | Kopelman et al. |
| 2006/0281041 A1 | 12/2006 | Rubbert et al. |
| 2007/0081718 A1 | 4/2007 | Rubbert et al. |

\* cited by examiner

METHOD FOR MANIPULATING A DENTAL VIRTUAL MODEL, METHOD FOR CREATING PHYSICAL ENTITIES BASED ON A DENTAL VIRTUAL MODEL THUS MANIPULATED, AND DENTAL MODELS THUS CREATED

CROSS-REFERENCE

This application is a continuation of U.S. application Ser. No. 13/227,435 filed Sep. 7, 2011, which is a continuation of U.S. application Ser. No. 12/654,762, filed Dec. 31, 2009 (now U.S. Pat. No. 8,041,439, which is a continuation of U.S. application Ser. No. 12/222,287, filed Aug. 6, 2008 (now U.S. Pat. No. 7,734,368), which is a continuation of U.S. application Ser. No. 11/349,124, filed Feb. 8, 2006 (now U.S. Pat. No. 7,555,403), which claims the benefit of prior U.S. Provisional Patent Application No. 60/699,499, filed Jul. 15, 2005, the contents of each of which are hereby incorporated by reference in their entirety.

FIELD OF THE INVENTION

This invention relates to dentistry and in particular to computer-aided methods associated with prosthodontics.

BACKGROUND OF THE INVENTION

There are many procedures associated with the oral cavity in which a precise three-dimensional representation of the cavity is very useful to the dental practitioner.

Such representations enable the practitioner to study the cavity of individual patients in a similar manner to the study of the traditional plaster model. More importantly, three-dimensional numerical entities of the dental cavity also allow the practitioner to study methods or approaches when dealing with particular dental problems of any given patient, and for the design of physical entities in relation therewith. For example, in prosthodontics, a computer model of a patient's teeth may be manipulated to provide machining data to manufacture a physical model of the intra oral cavity, and/or to design and manufacture a coping and/or a prosthesis.

A parameter used in the design and manufacture of a dental prosthesis, such as a crown or bridge, is the finish line, or transition boundary between the prosthesis and the dental preparation, and this needs to be precisely defined in three-dimensions. Obtaining the finish line coordinates from a computer virtual model is more efficient and often more accurate than from a plaster cast, and moreover facilitates the production of such a prosthesis, for example via CNC machining, rapid prototyping, or other computerized technologies, if desired.

However, it is often the case that when scanning the intra oral cavity to obtain 3D data of the preparation and finish line on which the virtual model is based, part of the finish line, and possibly also the shoulder and other parts of the preparation, may be obscured by soft tissues such as the gum that, no longer being pushed by the dental surfaces that have been removed, deform to cover at least a part of the finish line on the prepared dental site.

Additionally or alternatively, part or all of the finish line may be obscured by other agents, including, for example, accumulation of one or more of saliva, blood, lubricant used with a dental drill, debris resulting from working the, dental site, and so on.

SUMMARY OF THE INVENTION

Herein, "dental material" refers to any material associated with dental structures of the intra oral cavity, including but limited to natural dental materials such as for example enamel, dentine, pulp, dental roots, and non-natural dental materials such as for example metallic and non-metallic fillings, restorations, crowns, bridges, copings, preparations, and so on.

Herein, "dental clinic" refers to the interface between a dental practitioner and a patent, and thus includes any physical entity, in particular a clinic, in which there is interaction between a dental patient and a dental practitioner. While "dental practitioner" typically refers to a dentist, doctor or dental technician, it also includes herein all other caregivers, including for example dental surgeons, orthodontists, prosthodontists, or any other caregiver that may interact with a dental patient during the course of a dental treatment, or that may be involved in determining, preparing or providing dental treatment to a patient, particularly prosthodontic treatment. While "dental patient" or "patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, or veneering, or any other artificial partial or complete denture.

The term "virtual", applied herein with respect to models, manipulation of models, and so on, for example, refers to being created, simulated, or carried out by means of a computer or computer network or the like.

While the term "preparation" typically refers to the stump and including the finish line and shoulder that is left of the tooth that is to be replaced by the prosthesis—typically a crown—and on which the crown is to be mounted, the term herein also includes artificial stumps, pivots, cores and posts, or other devices that may be implanted in the intraoral cavity in such a position or in a position that is optimal for implanting the crown.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "numerical entity" is used herein synonymously with virtual model, 3D model, and other such terms, and relates to a virtual representation in a computer environment of a real object, such as for example a dentition or at least a part of intraoral cavity, or of a real model thereof The term "physical entity" is used herein to refer to a physical dental object included but not limited to a physical dental model of part or all of the dentition of the intraoral cavity including dies, a coping, a prosthesis, and so on.

The term "scanning" and its analogues refer to any procedure directed at obtaining 3D topographic data of a surface, particularly of a dental surface, and thus includes mechanical methods, typically based on 3D probes for example, optical methods, including for example confocal methods, for example as disclosed in WO 00/08415, the contents of which are incorporated herein in their entirety by reference, or indeed any other method.

The terms "tool" and "machining tool" are taken herein to include any tool that is adapted for material removal, and may include inter alia mechanical tools such as drills for example, laser tools such as for example laser drills or cutters, ultrasonic tools such as for example ultrasonic cutters, and so on.

Preferably, the machining paths and material removal characteristics of such tools can be finely controlled, typically by computer means.

The present invention relates to a method for manipulating a virtual dental model, comprising:
(a) providing a 3D virtual model of at least a portion of an intraoral cavity comprising a preparation having a finish line, wherein at least a portion of the finish line is obscured;
(b) manipulating said 3D virtual model in the vicinity of said obscured portion of said finish line in a virtual manner such as to create an auxiliary 3D virtual model corresponding to said obscured portion of said finish line;
(c) providing topographical data of the finish line from the virtual model and the said auxiliary virtual model.

The virtual model may be provided by scanning the intraoral cavity in vivo, or by any other suitable method.

The finish line may be partially or fully obscured by any obscuring entity or matter, including, but not limited to, deformed soft tissues, accumulation of one or more of saliva, blood, lubricant used with a dental drill, debris resulting from working the dental site, and so on.

The method can further comprise:
(d) identifying in said 3D virtual model a first virtual model part representing a dental site comprising said preparation and a second virtual model part representing at least soft tissues in abutting virtual contact with said first virtual model part;
(e) manipulating said 3D virtual model such as to separate said first virtual model part from said second virtual model part;
(f) manipulating said first virtual model part such as to create said auxiliary virtual model.

Step (d) may be carried out substantially in an automated manner when said 3D virtual model provided at step (a) comprises color data associated with 3D topographic data, wherein said identification of said first virtual model part and said second virtual model part is based on color differences therebetween.

The second virtual model part may comprise said obscured portion of said finish line.

The step of manipulating said first virtual model part such as to create said auxiliary virtual model corresponding to said obscured part of said finish line may comprise:
(g) providing at least one cross section of said 3D virtual model along a working plane inclined to the occlusion plane, at least within said obscured finish line portion, said cross-section comprising a first cross-section profile representing said preparation and a second cross-section profile representing obscuring matter in abutting virtual contact with said first cross-section profile at a contact region;
(h) extrapolating said first cross-section profile from said contact region to provide a third cross-section profile representing at least an approximation of a corresponding cross-section of said dental site below said obscuring matter and identifying therein a corresponding element of said obscured finish line portion.

By "extrapolating" is meant any suitable method, which may be numerical, graphical, intuitive, and so on, based on the first cross-section profile.

Optionally, additional data relating to the emerging profile, gum line and so on may also be provided.

In step (g), said at least one cross section of said virtual model may be provided along a corresponding plane inclined generally orthogonally to the occlusion plane.

Alternatively, the working planes may be parallel or non parallel one to another, and/or at any desired angle to the occlusal plane.

Alternatively, any other method, for example any suitable graphical method, may be used for defining the geometry of at least the obscured finish line portion.

The method optionally further comprises creating a trimmed first model part comprising said first model part and said auxiliary virtual model, and also manipulating said second model part to remove surface data thereof corresponding to said auxiliary virtual model and creating a trimmed second model part.

The said trimmed first model part can be further manipulated such as to include a virtual model base projecting therefrom, and said trimmed second model part can also be manipulated such as to include a model well substantially complementary to said model base. The virtual model base may optionally comprises a depth dimension extending substantially orthogonally to an occlusial plane of the intra oral cavity, and said virtual model base may of substantially uniform cross-sectional profile along a depth thereof. Alternatively, the base may be convex-shaped, conical, fustoconical, or any other suitable shape.

The perimeter of the virtual base, when viewed along said depth direction may correspond to any one of a finish line or demarcation line of the trimmed first model. Alternatively, the perimeter of the virtual base, when viewed along said plan direction, may correspond to any one of circle, oval, polygon or any suitable shape.

Optionally, one of said virtual model base and said virtual model well further comprises at least one virtual projection, and the other one of said virtual model base and said virtual model well further comprises a virtual socket structure for virtually receiving said at least one projection. In other words, the virtual socket is substantially complementary in form and size to the corresponding projection. The projection can also take the form of a laterally projecting tab that is receivable in a socket structure that is formed as a longitudinal channel on the side of the well.

The said at least one virtual projection and virtual socket structure are arranged with respect to said virtual base and virtual well such that said virtual base can be virtually received in said virtual well, in only one orientation with respect thereto.

The method optionally further comprises the step of preparing computer instructions for controlling operation of a computer controlled manufacturing machine for creating physical models corresponding to said trimmed first and second virtual model parts respectively including said virtual model base and said virtual model well. The said computer instructions may be directed to carrying out a material removal operation on at least one material blank to create said physical models, for example. This material removal operation may comprise CNC (Computer Numerical Control) machining including milling of said at least one material blank.

The present invention also relates to a method for manufacturing a dental model, comprising:
(a) providing a trimmed first virtual model part and a trimmed second virtual model part, according to the invention, corresponding to at least one dental site;
(b) preparing computer instructions for controlling operation of a computer controlled manufacturing machine for creating physical models corresponding to said trimmed first and second virtual model parts respectively including said virtual model base and said virtual model well; and (c) executing said computer instructions on said computer controlled manufacturing machine and creating a set of physical models comprising a trimmed first physical model part and a trimmed second physical model part corresponding to said trimmed first and second virtual model parts respectively including said virtual model base and said virtual model well.

A dental site relates to a location in the intra oral cavity comprising one or more teeth of interest. One or more such teeth may include a preparation.

The computer instructions may be directed to carrying out a material removal operation on at least one material blank to create said physical models. The material removal operation may comprise CNC machining of said at least one material blank.

The method for manufacturing a dental model may be applied to a single dental site, or alternatively to a plurality of dental sites on at least one jaw of an intra oral cavity Inn the latter case particularly, the trimmed second virtual model corresponding to each said dental site can be suitably joined in a virtual manner to provide a global virtual model of said jaw. In such a manner it is possible to manufacture a model of one or both partial of full jaws, in which any number of the teeth therein, whether or not they have a preparation, are formed as separate models which can be removed and replaced in the jaw model. Tooth models in cases where then tooth is complete or in which there is no obstruction can be manufactured in a similar manner as described above, mutatis mutandis, with the main differences that no recreation or reconstruction of obscured portions thereof need to be performed.

The invention also relates to a method for at least one of designing and manufacturing a dental coping, using a trimmed first virtual model according to the invention.

The invention also relates to a method for at least one of designing and manufacturing a dental prosthesis, using a trimmed first virtual model according to the invention.

The invention also relates to a physical model set of at least a portion of an intra oral cavity, comprising a trimmed first physical model part and a trimmed second physical model part corresponding to a trimmed first virtual model part and a trimmed second virtual model part according to the invention.

The present invention also relates to systems for manipulating virtual dental models and for manufacturing physical dental entities based on a virtual dental model manipulated according to the invention. Such systems may include a microprocessing unit comprising suitable software for carrying out the method of the invention, an interface, such as for example a mouse, tablet, keyboard and so on, a display, and a data input module for inputting 3D data of the intra oral cavity.

Thus, according to the invention, a 3D virtual model of an intra oral cavity in which at least a part of a finish line of a preparation is obscured is manipulated in virtual space by means of a computer or the like to create, recreate or reconstruct finish line data and other geometrical corresponding to the obscured part. Trimmed virtual models, and trimmed physical models, can then be created utilizing data thus created. The virtual models and/or the physical models may be used in the design and manufacture of copings or of prostheses.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
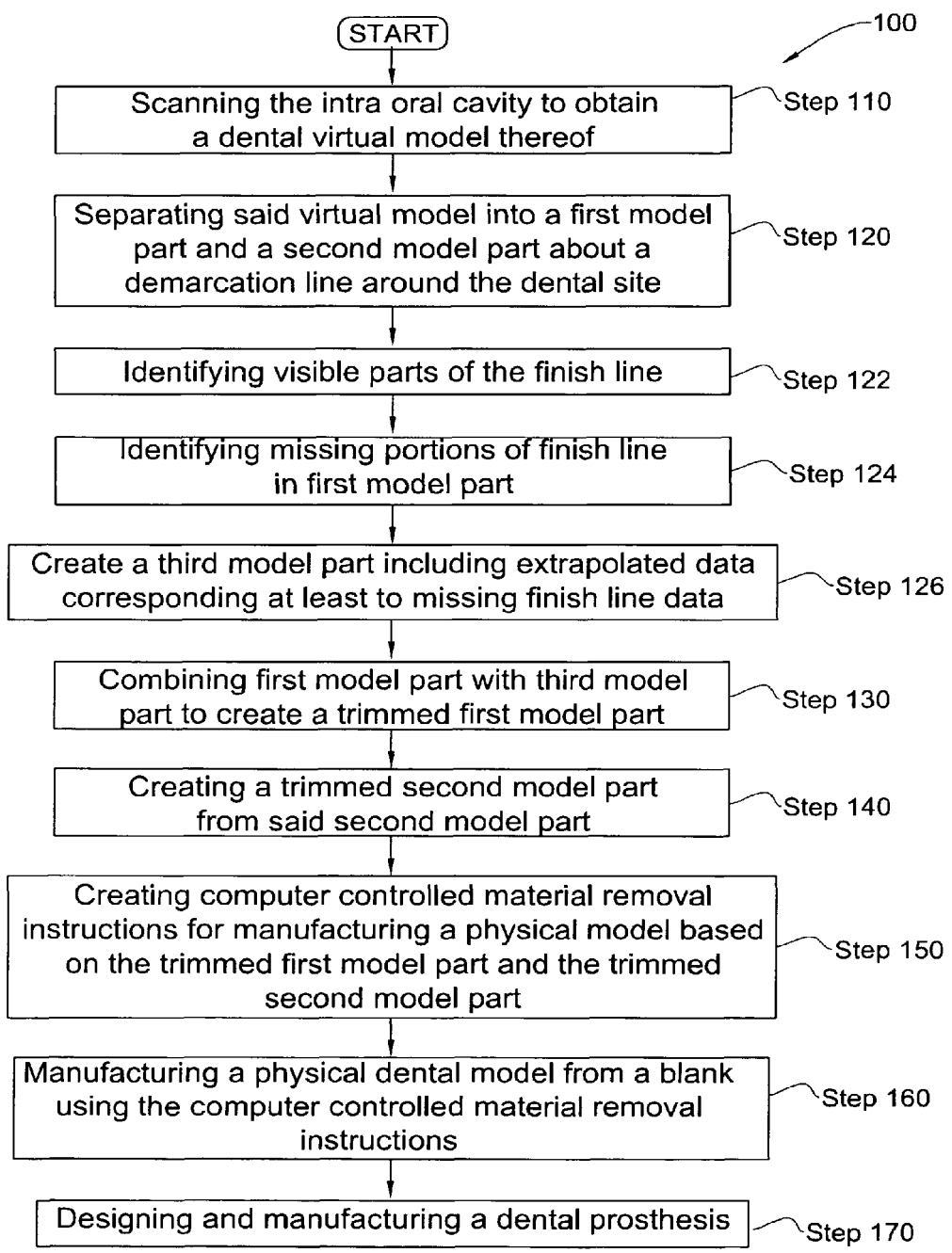
FIG. 1 shows, by way of a flow chart, a method for manipulating a dental virtual model in accordance with an embodiment of the invention.

A computer-based method for manipulating a virtual dental model, particularly useful for defining a finish line (also referred to herein as "margin line"), according to the invention is illustrated in FIG. 1. Accordingly, acquiring an accurate 3D representation (herein also referred to as "three-dimensional model", "3D model", "virtual model" and the like) of the intraoral cavity is the first step 110 that is carried out by the method 100. This first virtual model is generally designated with the numeral 500 in the accompanying figures.

The target parts of the intraoral cavity that are to be scanned are first identified. The target parts are the parts (also referred to interchangeably as zones or areas) of the intraoral cavity 200 which form the focus of a particular dental procedure for a particular patient and regarding which it is desired to obtain the 3D topographical or surface data thereof. The target parts typically include the part of the tooth or the teeth on which a particular prosthodontic procedure is to be performed, and in some cases may include partial or the full mandibular or maxillary arches, or both arches. For example, the procedure may be a prosthodontic procedure involving a crown or bridge prosthesis to be designed and fabricated for fitting onto a preparation at a particular dental site.

Figure 3:
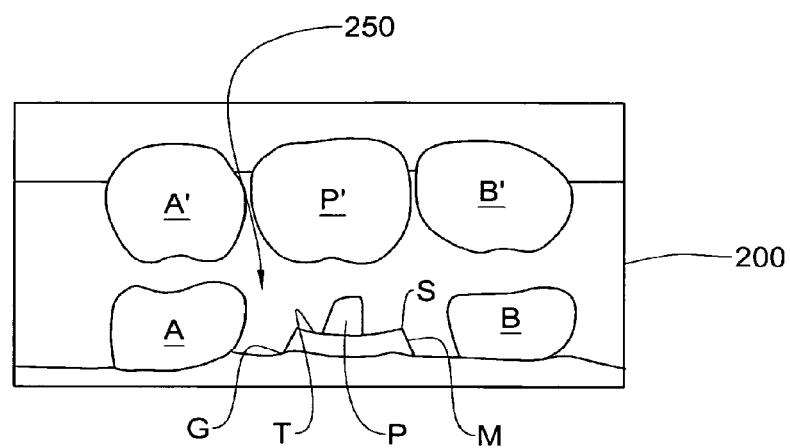
FIG. 3 schematically illustrates a portion of the intra oral cavity requiring a prosthesis.

The method of the invention may be applied after the dental site 250 has been prepared, at least partially for a prosthesis. For a crown prosthesis, the dental site 250 includes a single tooth that is prepared for receiving the prosthesis, while for a bridge prosthesis, there are typically two dental sites, each of which includes a tooth that needs to be prepared, in order to anchor the prosthesis. Referring to FIG. 3, the preparation of each tooth requires the dental practitioner to perform a dental material removal operation at the dental site 250, creating a preparation P having a central anchoring stump joined via shoulder T to a finish line S that circumscribes the stump and separates the preparation from the emerging profile M, which in turn extends to the gum line G.

When the target area including the dental site 250 is scanned very accurately, it is possible for the internal surface of a corresponding coping to be correspondingly accurately designed. Ancillary parts of the intraoral cavity are also typically included in the scan, and comprise parts of the adjacent and opposed teeth, principally teeth A, B, P', and often to a lesser extent teeth A' and B' (which are adjacent to the opposite tooth P') or parts thereof. Typically, but not necessarily, the resolution of the scanned data for the ancillary parts may be less than for the dental site itself, since the manufacturing accuracy required for the external surfaces of the crown prosthesis (the design of which is dependent on the dental surfaces of the ancillary parts) may be substantially less than for the internal surface of the coping (or of the crown if this is monolithic).

Figure 4:
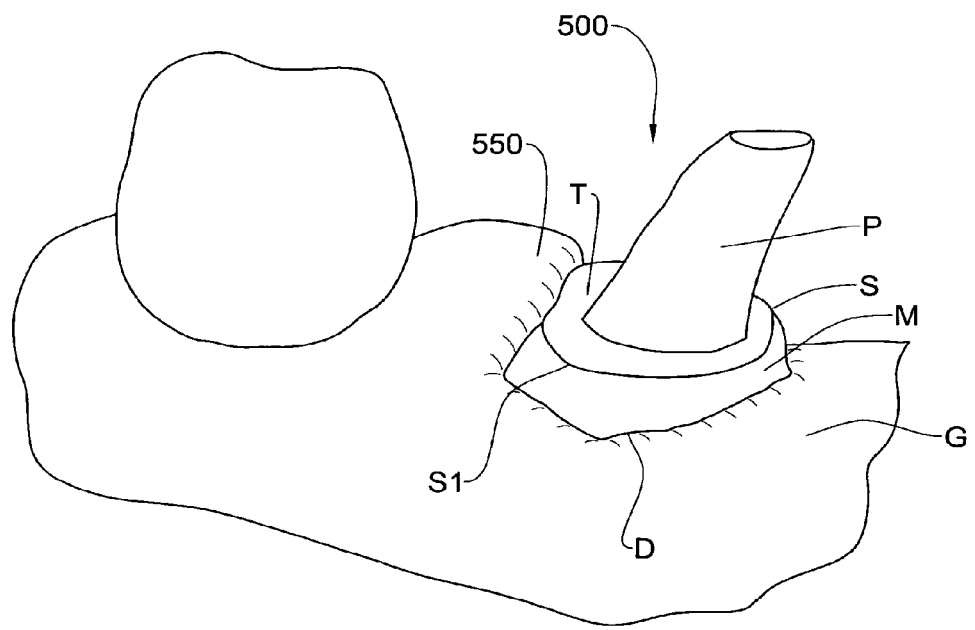
FIG. 4 illustrates a virtual model of the intra oral cavity as viewed with 3D attributes.

The present invention is particularly applicable to situations in which at least a part of the finish line S and possibly a part of the shoulder T is obscured by other material 550, typically either soft tissue (typically gums) and/or a retraction wire (FIG. 4) and/or other foreign matter. Thus, the virtual model 500 obtained by the scanning process lacks finish line data (and also emerging profile data) at the obscured portions of the finish line.

Figure 2:
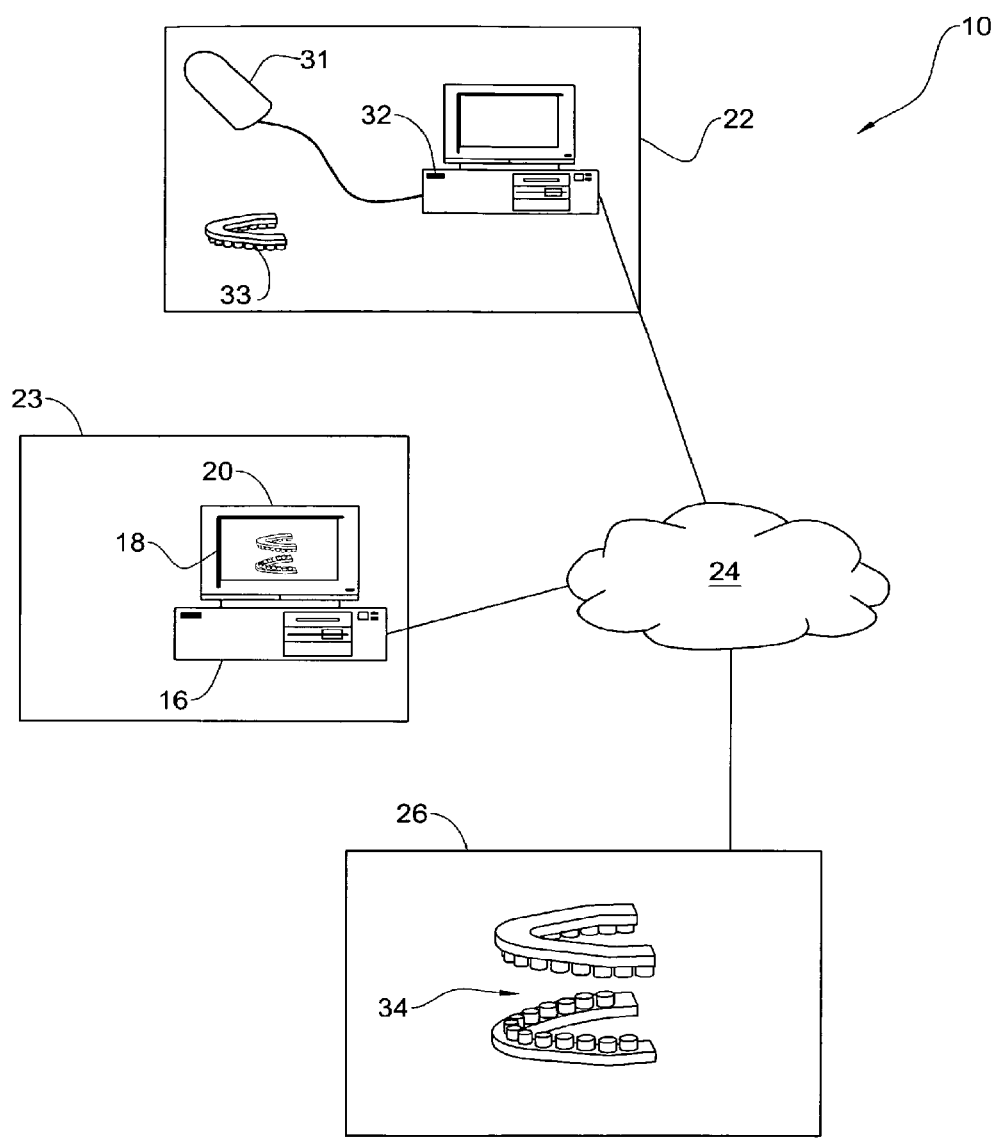
FIG. 2 shows various elements of a system used for providing and manipulating a virtual dental model according to the invention.

The 3D digitized data of the intraoral cavity, including the dentition and associated anatomical structures of a patient, may be provided using any suitable equipment for scanning a patient's teeth. Referring to FIG. 2, this is usually done at a dental clinic 22 by the dentist or other dental practitioner. The dental clinic 22 is typically linked to one or more dental labs 26, and possibly also to a dental service center 23 via a communication means or network such as for example the Internet or other suitable communications medium such as an intranet, local access network, public switched telephone network, cable network, satellite communication system, and the like, indicated by the cloud at 24. The dental lab 26 is particularly adapted for defining the finish line, as well as for other tasks such as designing prostheses, designing and manufacturing physical models of the dentition, and possibly also for manufacturing at least an external profile of the prostheses. The dental service center 23 is particularly adapted for manufacturing dental hardware that requires a very high degree of precision, for example inner surfaces of prostheses that are required to match external surfaces of copings, and possibly also the copings themselves.

Such scanning equipment may include any suitable optical scanner, for example, a hand-held scanner 31 that is used by the practitioner to acquire the 3D data. Advantageously, a probe for determining three dimensional structure by confocal focusing of an array of light beams may be used, for example as manufactured under the name of CB-CAD or as disclosed in WO 00/08415, the contents of which are incorporated herein by reference in their entirety. The 3D data obtained by the probe may then be stored in a suitable storage medium, for example a memory in a computer workstation 32. Typically, the 3D data is sent over a suitable communication network 24 to the dental lab 26, for further processing, as described below. Optionally, the to the dental service center 23 the 3D data may be sent via communication network 24 to the dental lab 26, for the further processing.

Optionally, and preferably, color data of the intraoral cavity is also provided together with the 3D data, and thus the virtual model comprises coordinates and color information of the dental surfaces scanned. Examples of such scanners are disclosed in co-pending application entitled "METHOD AND APPARATUS FOR COLOUR IMAGING A THREE-DIMENSIONAL STRUCTURE", filed on 17 Jun. 2005 and published under US 2006-0001739, and which is assigned to the present Assignee. The contents of the aforesaid co-pending application are incorporated herein by reference in their entirety.

Alternatively, the clinic 22 may include equipment for obtaining a negative casting of a patient's teeth. In this case, the negative cast or impression is taken of the patient's teeth, in a manner known in the art, and this negative model 33 is dispatched to one of the dental labs 26 that is equipped to prepare from the negative model a positive cast 34 suitable for scanning The positive cast 34 may be scanned at the dental lab 26 by any method known in the art, including using the aforesaid probe manufactured under the name of CB-CAD or as disclosed in WO 00/08415. The 3D data is then transmitted over the network 24 to the service center 23. Alternatively, the positive cast 34 may be dispatched to the service center 23 by the dental clinic 22 and scanned at the service center to obtain the 3D data. Alternatively, the service center 23 produces a positive model 34 from the negative model 33 and is scanned thereat, or sent to the dental clinic 22 to be scanned thereat. Alternatively, the negative model 33 is scanned, either at the dental lab 26 or at the service center 23.

Alternatively, the negative model 33 provided by the clinic 22 is sent to the service center 23, either directly by the clinic 22, or indirectly via the dental lab 26, and a composite positive-negative model may be manufactured from the original negative model. Thereafter, the positive-negative model may be processed to obtain 3D digitized data, for example as disclosed in U.S. Pat. No. 6,099,314, assigned to the present Assignee, and the contents of which are incorporated herein in their entirety.

Alternatively, the 3D digitized data may be obtained in any other suitable manner, including other suitable intra oral scanning techniques, based on optical methods, direct contact or any other means, applied directly to the patient's dentition. Alternatively, X-ray based, CT based, MRI based, or any other type of scanning of the patient or of a positive and/or negative model of the intra-oral cavity may be used. The dimensional data may be associated with a complete dentition, or of a partial dentition, for example such as a preparation only of the intra oral cavity.

Once the 3D digitized data is obtained, the next steps 120-126, which are performed with the aid of a suitable computer, enable the full finish line S to be defined, which enables the subsequent design and manufacture of an appropriate dental prosthesis, step 170, to be followed by the installation of the appliance in the oral cavity of the patient, step 180. These steps are generally carried out in the dental lab 26, though may be executed at the dental clinic 22 or service center 23 with the appropriate equipment and expertise.

Figure 5:
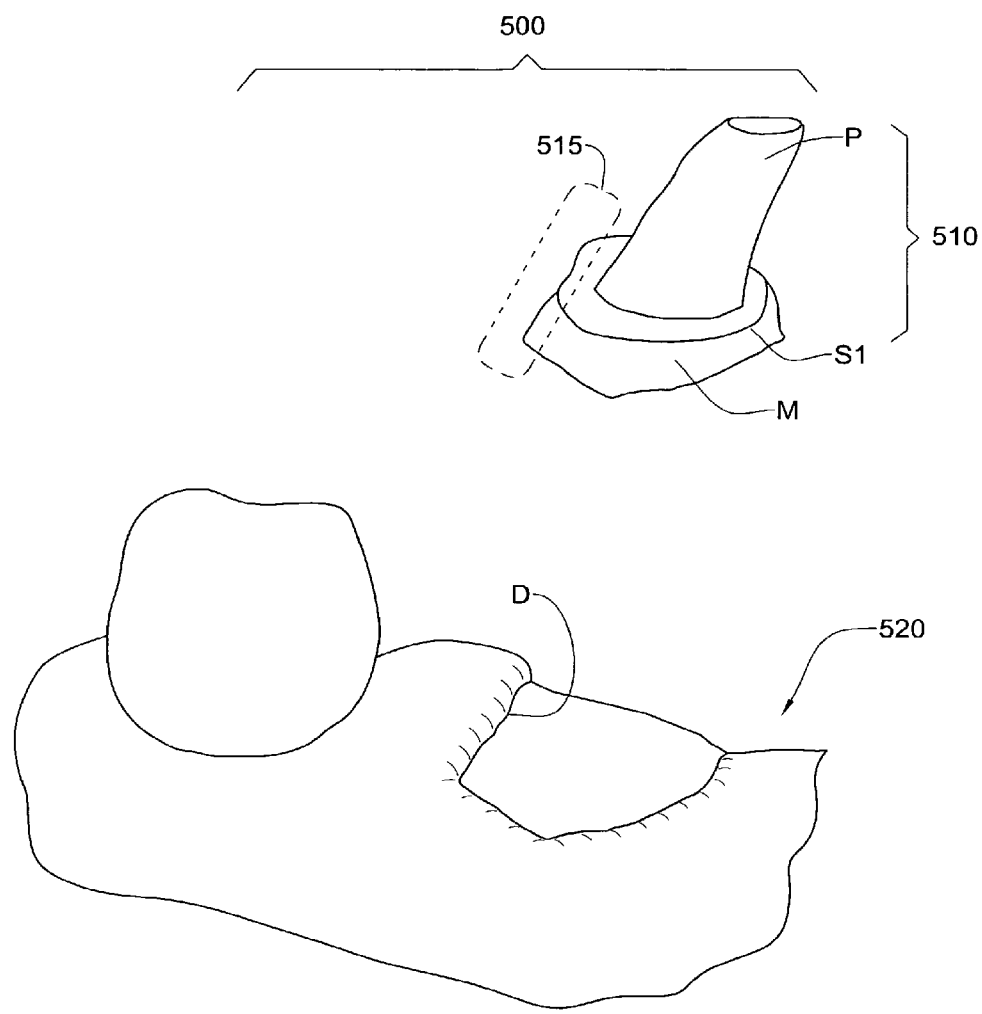
FIG. 5 illustrates the virtual model of FIG. 4 separated into a first model part and a second model part.

Referring to FIG. 1 and FIG. 5, in step 120 the virtual model 500 is manipulated by means of a suitable computer in order to separate a first part 510 of the virtual model representing the dental site 250, in particular the hard tissues thereof, from a second part 520 of the virtual model, typically the remainder of the model 500, and including at least the data representing the soft tissues and possibly foreign matter such as retraction wires, etc, that surround the first part 510. Thus, this step isolates the surface data corresponding to the parts of the emerging profile M, the portion S1 of finish line S and preparation P that are not obscured by soft tissue or foreign objects including, for example, saliva, blood, lubrication fluid, debris and so on. This step may be performed manually with a computer, typically interactively, by a user, by means of suitable graphics software, for example, that display model 500, and an interface such as a mouse, keyboard, and so on, for example. The user may visually identify a demarcation profile D (FIGS. 4 and 5) that separates model parts 510 and 520, and for this purpose the model 500 as displayed may be manipulated and viewed at any attitude, rotational angle, magnification etc. as desired. Suitable software for manipulating a virtual model in this manner are well known in the art and will not be described further herein. Then, the user virtually marks a number of points on the displayed model 500 which are converted by the computer into corresponding 3-dimensional coordinates of the demarcation profile, and suitable interpolation between points completes the definition of the demarcation profile D. Then, the computer can divide the model 500 along profile D into model parts 510 and 520.

Alternatively, and particularly when the virtual model 500 also comprises color data corresponding to the topographical data, the color differences between the relatively white hard dental surfaces of the dental site 250 and the relatively pink/red gum tissue and/or the retractor wire or other foreign matter, may be used to separate the model 500 into model parts 510 and 520 in an automated manner. Examples of such methods are disclosed in co-pending application entitled "METHOD FOR PROVIDING DATA ASSOCIATED WITH THE INTRAORAL CAVITY", filed on 17 Jun. 2005 and published under US 2005/0283065, and which is assigned to the present Assignee. The contents of the aforesaid co-pending application are incorporated herein by reference in their entirety.

Figure 6:
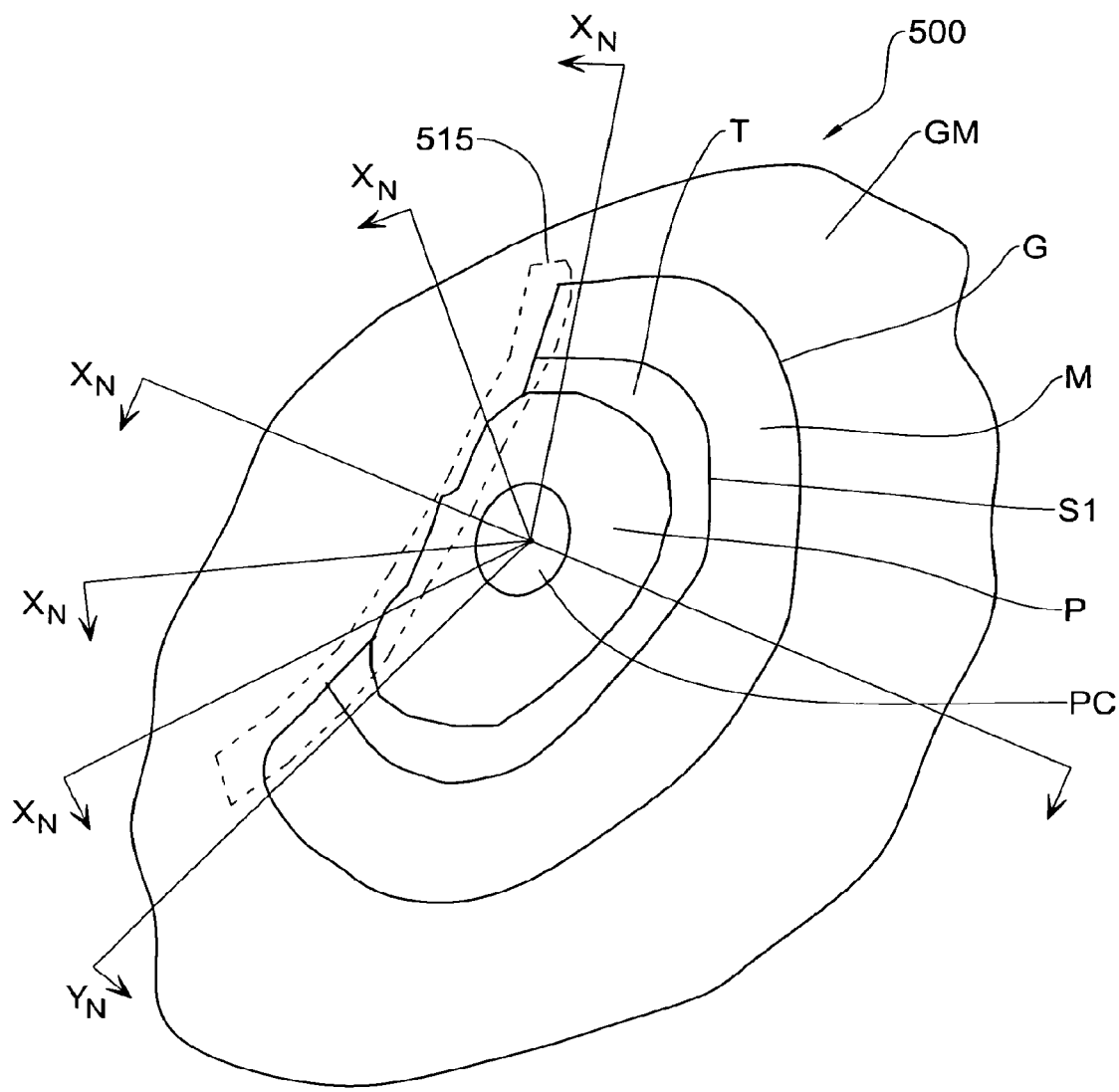
FIG. 6 illustrates in plain view the first model part of FIG. 5 including a plurality of planes normal to this view.

In the next step 122, and referring also to FIGS. 5 and 6, the exposed portions S1 of the finish line S, i.e., the portions that are visible, are identified and marked in the first model part 510. By "marking" is included that an attribute is added to the data points corresponding to these portions of the model 510, so that these portions may be highlighted and/or further manipulated, displayed etc. as a unit. This identification and marking may be done manually, by means of a display and interface, similarly to that described for step 120 above, mutatis mutandis. Alternatively, for example, this may be accomplished in an automated manner, or at least semi-automated manner, by suitably manipulating the first model part 510 by means of a suitable algorithm or the like. For example, the computer in which the method is being executed may be programmed to identify within the data of the first model part 510, relatively sharp changes in geometry, as is the case in the change of cross-sectional profile between the emerging profile M, the finish line S and shoulder T. Alternatively, other rules may be incorporated to provide the exposed portions S1 of the finish line S.

In the next step 124, the areas of the first model part 510 that do not include a finish line are identified and optionally marked. This identification and marking may be done manually, by means of a display and interface, similarly to that described for step 122 above, mutatis mutandis. Alternatively, the computer may attempt to determine in what manner the exposed portions S1 does not complete a closed geometrical form, and thus determines which parts of the geometric form are "missing". The computer can then compute in an automated manner which part of the 3-dimensional space generally occupied by the first model part 510 would include these "missing" parts.

In any case, once the missing portions, herein generally designated as 515, are identified and optionally marked in a suitable with reference to the first model part 510, the next step 126 is to create 3-dimensional representations of the missing portions 515, i.e., a third model part. This can be accomplished in a number of different ways. For example, and referring to FIGS. 6 and 7, the virtual model 500 is sliced about a plurality of working planes $X_N$ to provide a corresponding plurality of cross-sections CN of the model 500. These cross-sectional planes XN are typically orthogonal to the occlusal plane, and preferably pass approximately through the center portion PC of the preparation P. The plurality of planes may span an arc as viewed from above the dental site (FIG. 6) such as to include the full missing portion 515 and extend at least a little beyond the same to include at least two cross-sectional profiles that fully include emerging profile M data, finish line S data, preparation P data, gum line G data, plus gum GM data.

Figure 7:
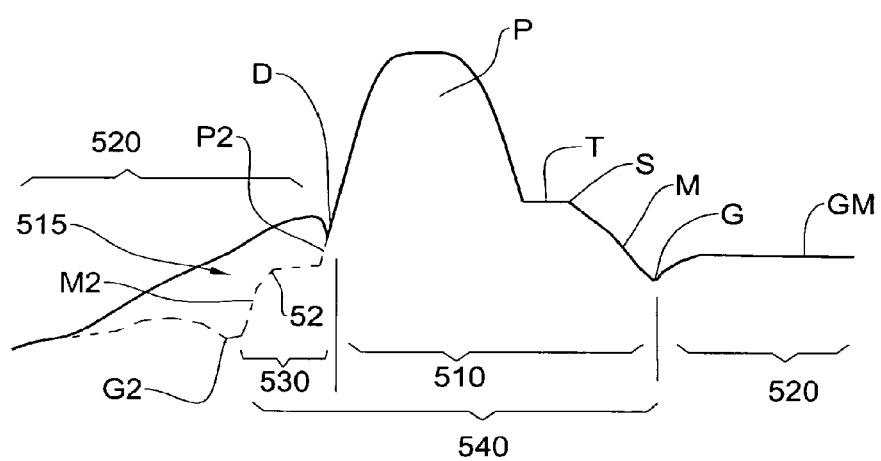
FIG. 7 illustrates a typical cross-section of the virtual first model part obtained along one of the planes in FIG. 6.

A typical cross-section $C_N$ is illustrated in FIG. 7, and shows the profile of the model 500, including first model part 510, second model part 520, and demarcation line D. Based on the user's experience and skill, the user can extrapolate where he or she considers that at least one or more of the missing finish line $S2_N$ data, missing emerging profile data M2, missing preparation data P2, and missing gum line data G2 data may be in relation to this cross-section. These missing data can then be input to the computer in which the manipulations are being carried out, for example by "clicking" with a mouse or by means of a tablet, or by any other computer aided means, at locations on the displayed cross-section where the extrapolations are to be made. Such extrapolations may be made by the user, utilizing experience and judgment as to where the missing profile may be. Alternatively, the user, knowing what type of tool was used for creating the preparation, may have a fair idea of the profile of the finish line cross section. For example, the finish line may be of any type thereof, for example knife edge, feather edge, chamfer, chamfer bevel, shoulder, shoulder bevel, and so on. Alternatively, the finish line may comprise a combination of different types around the periphery of the preparation, for example part of the finish line for a particular preparation may be knife edge, while another part may be feather edge. According to the type of finish line the user is expecting to find, the same type of profile may be applied to the missing section, and subsequently modified, manually or automatically using any suitable matching, smoothing, graphical or other type of algorithm to fit as required.

When this operation has been repeated for all the cross-sections, a 3-dimensional virtual third model part 530 corresponding to the extrapolated data may be created by the computer by properly integrating the created data, and the user may view the results together with or separately from the first model part 510.

Alternatively, the planes $X_N$ may be at any orientation and at any position with respect to the virtual model 500.

Alternatively, the missing portions may be virtually extrapolated using any suitable graphic based technique, for example, or in any other suitable manner.

In other cases, it is possible for a number of portions of the finish line to be obscured, and these portions are each treated as described above, mutatis mutandis in order to extrapolate and obtain the missing 3D data.

In some cases it is possible that the full extent of the finish line S is in fact obscured, and in such cases the method of the invention is applied for the full perimeter around the preparation P in a similar manner to that described above, mutatis mutandis, the main difference lying in that the sections $C_N$ would need to intersect the full perimeter circumscribing the preparation P.

In other case, it is possible for the finish line S to be exposed, but for a part or all of the emerging profile to the obscured. Again, the same method as above may be employed to obtain the missing 3D data, mutatis mutandis.

Alternatively, step 126 may be performed in a fully automated or semi automated manner, and suitable algorithms and/or rules such as geometrical rules may be formulated for this purpose. In any case, according to the invention, the third model part 530 may be refined over and over again until a suitable result is achieved. At each iteration, the user may inspect the third model part 530, and perhaps finely tune control parameters of the algorithm, for example, to arrive at a better solution.

In the next step 130, the third model part 530 is combined together with the first model part 510 in a virtual manner to create a completed trimmed virtual first model part 540 of the dental site, including a fully defined finish line S and preferably also a complete emerging profile M.

Figure 8:
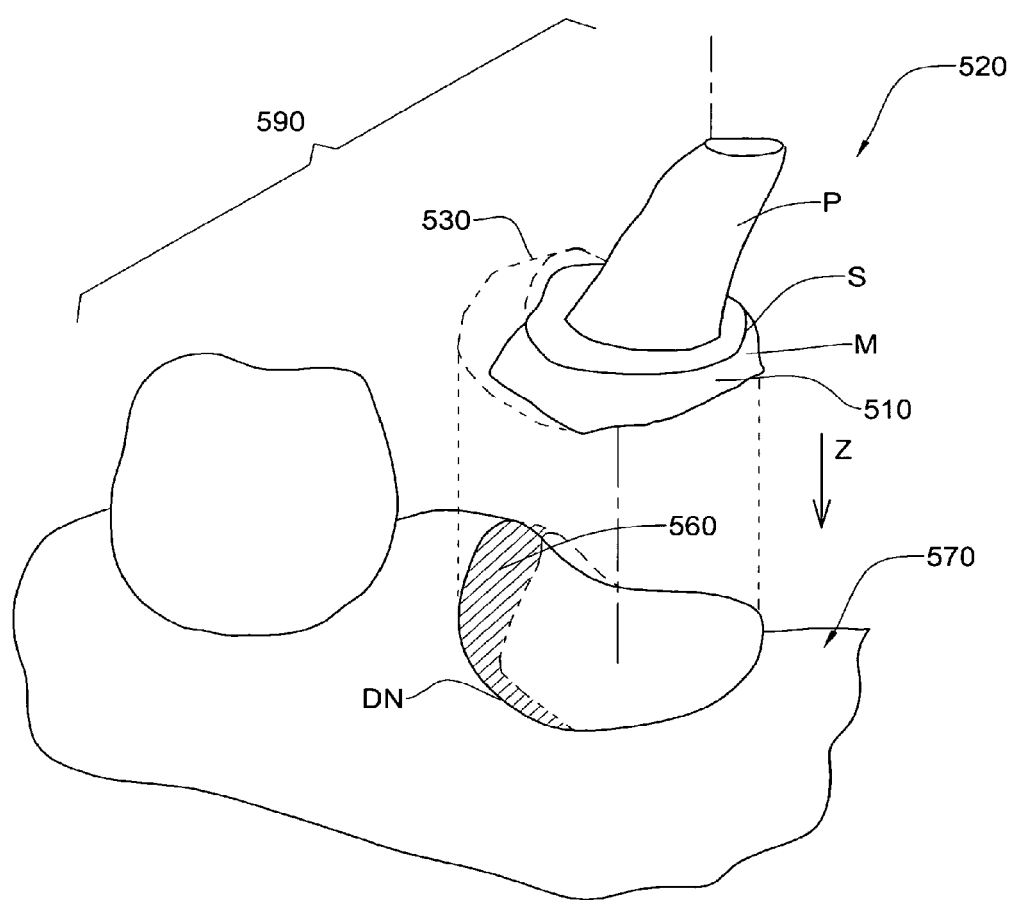
FIG. 8 illustrates the model parts of FIG. 5 after having been virtually trimmed according to the invention.

In the next step 140, and referring to FIG. 8, the second model part 520 is converted to a trimmed second model part 570 by manipulation thereof so as to effectively remove thereof excess surface data 560 that corresponds to the third model part 530, i.e., that would be superposed along a particular direction Z when joining the complete virtual model 540 to the second model part 520 such that the data corresponding to the first model part 510 in said trimmed first model part 540 "fits" in the same position as before with respect to the second model part 520. Direction Z is typically substantially orthogonal to the occlusion plane. The trimmed second model part 570 thus joins, at new demarcation line DN (at least along direction Z), the trimmed first model part 540 to form a new virtual model 590 in which the finish line S, emerging profile P, gum line G and preparation P are now fully defined.

For the case of a bridge prosthesis, the procedure may be repeated, if required, for each of the anchoring teeth.

Figure 9:
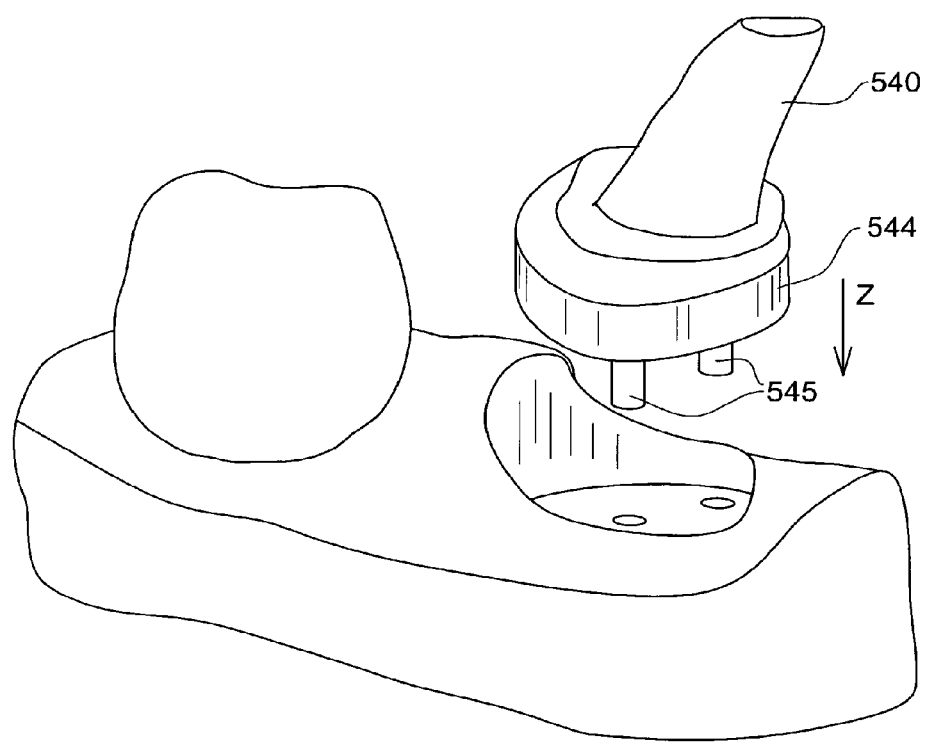
FIG. 9 illustrates a physical model of the intra oral cavity based on the trimmed virtual model of FIG. 8.

The method of the invention may be further extended to the manufacture of a physical dental model that may be used in the design and/or manufacture of a prosthesis, for example a crown or bridge prosthesis. Thus, in step 150, the trimmed first virtual model part 540 is modified to include a virtual base portion 544, typically having a cross-sectional profile identical to a plan cross-section of the complete virtual model 540 as viewed in direction Z (FIG. 9). Then, machining instructions, typically CNC milling instructions, but alternatively including any suitable computer instructions for a computer controlled material removal machine, for a material removal operation are created based on the thus modified trimmed first model part 540. The machining instructions may be further modified to include instructions for forming alignment plug members 545 extending from the bottom part of the base portion 544.

Similarly, in step 150 the trimmed second model part 570 is modified to include a well portion 574, typically having a cross-sectional profile identical to a plan view of the new demarcation line DN as viewed in direction Z, and machining instructions, typically CNC milling instructions, but alternatively including any suitable computer instructions for a computer controlled material removal machine, for a material removal operation are created based the thus modified trimmed second model part 570. Alternatively, in another aspect of the invention, rather than material removing instructions, computer instructions for creating a physical model using rapid prototyping techniques may instead be created. The machining instructions may be further modified to include instructions for forming alignment sockets 574 complementary to receiving members 545.

In general, the shape of the demarcation line, in plan or occlusal view, is asymmetric, and therefore the trimmed first model part 540 will generally fit in the trimmed second model part 570 in only one, the correct, orientation. Thus, in many cases it is possible to do without the plug members 545 and alignment sockets 574.

In any case, the base portion 544 is generally complementary to the well portion 574.

Alternatively, the trimmed first model part 540 may be based on the finish line, rather than the demarcation line, so that in plan view the outer profile of the trimmed first model part 540 corresponds to the finish line. Similarly, the profile of the well portion 574 in plan view also corresponds to the finish line, or close thereto to allow a small clearance between the trimmed first model part 540 and the trimmed second model part 570.

Alternatively, the trimmed first model part 540 may base portion 544 that is a independent of the finish line or the demarcation line, but rather circumscribes both, so that in plan view the outer profile of the trimmed first model part 540 may comprise, for example, a circle, oval, polygon, and so on. Similarly, the profile of the well portion 574 in plan view also generally corresponds to outer profile of the trimmed first model part 540. When the outer profile of the trimmed first model part 540 comprises a symmetrical shape, it may be necessary to include plug members 545 and alignment sockets 574.

Once the computer based instructions for creating the physical models are ready, the physical models corresponding to the trimmed first model part 540 and the trimmed second model part 570 may be created in a corresponding manner.

To manufacture a prosthesis such as a crown or a bridge, for example, the lab technician requires two physical jaws models mounted on an articulator or placed in the correct spatial orientation one against the other. According to the present invention, the computer controlled material removal instructions also take into consideration also the spatial relation between the two jaws and their occlusion, for example as disclosed in WO 2004/030565 assigned to the present Assignee, and the contents of this publication are incorporated herein in their entirety.

In the next step 160, a material removal operation is performed by a computer aided removal operation machine having a suitable machining tool, using any suitable CAM (Computer Aided Manufacturing) technology, typically a CNC milling machine, on a blank of material. This material is typically plaster or any other type of material commonly used for dental models, however any other suitable material may be used.

Alternatively, other techniques may be used, for example rapid prototyping, for creating the physical models. Accordingly, a physical model of the two jaws or at least a part of each of the two jaws corresponding to the virtual model 500 is manufactured, together with suitable alignment structures that ensure the proper occlusion relationship between the two components of the model representing the two jaws or the two jaw fragments.

At this point, the technician has his necessary physical model and can proceed with making the crown or the bridge.

Optionally, the physical model may be designed and manufactured comprising a plurality of individual detachable tooth models, including the target tooth, and any one or more of the surrounding and facing teeth. Similarly, when providing a physical model for use in connection with a bridge, the tooth models of one or both of the anchor teeth may be detachable from the model jaw (partial or full), and optionally, any one or more of the surrounding and facing teeth may also be detachable. When more than one tooth is detachable in the model, it is ensured that the profile of the base portion for each detachable tooth model is sufficiently different from the other base portions, and/or different plug member/alignment socket arrangements are used, to reduce the possibility of the wrong tooth model being matched with a particular well.

In step 170, and based on information from the virtual 3D image, the dentist or a technician may generate a 3D virtual prosthesis model of a crown to be fitted on a tooth stump or of a bridge to be fitted on the tooth surface, to generate a digital file. Alternatively, the outer surface of the prosthesis may be designed manually if desired. Optionally, and typically, the prosthesis model may also include a virtual model of a coping plus a virtual model of a cap that is to be mounted onto the coping. The coping may be manufactured using any suitable method, for example as disclosed in WO 2004/087000, also assigned to the present Assignee, and the contents of which are incorporated herein in their entirety. The cap or full prosthesis may be manufactured using any suitable method, for example as disclosed in U.S. Ser. No. 11/046,709 or in U.S. Provisional Application No. 60/632,350, also assigned to the present Assignee, and the contents of which are incorporated herein in their entirety.

In the final step, the prosthesis may be installed in the oral cavity of the patient.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. A system for manipulating a virtual dental model, the system comprising a computer having instructions that, when executed, cause the computer to:
    receive a 3D virtual model of a dental site comprising dental surfaces, wherein a first portion of the dental site is obscured by a material;
    manipulate the 3D virtual model to create an auxiliary 3D virtual model that includes a representation of the first portion of the dental site in which the first portion is not obscured by the material; and
    provide topographical data of the first portion from the virtual model and the auxiliary virtual model so as to reconstruct data of the first portion of the dental site.

2. A system according to claim 1, wherein the manipulate step comprises separating the 3D virtual model into a first virtual model part representing a preparation and a second virtual model part representing soft tissues proximate the preparation of the first virtual model part.

3. A system according to claim 2, wherein the 3D virtual model of the dental site comprises color data associated with 3D topographic data, and separating the first virtual model part and the second virtual model part is based at least in-part on color differences in the 3D virtual model.

4. A system according to claim 2, wherein the second virtual model part comprises an obscured portion of a finish line.

5. A system according to claim 2, wherein the manipulate step further comprises creating a trimmed first model part comprising the first virtual model part and the second virtual model part.

6. A system according to claim 5, wherein the manipulate step further comprises removing surface data from the second model part to create a trimmed second model part.

7. A system according to claim 6, wherein the trimmed first model part includes a virtual model base and the trimmed second model part includes a model well substantially complementary to the virtual model base.

8. A system according to claim 7, wherein the virtual model base comprises a depth dimension extending substantially orthogonally to an occlusal plane of an intraoral cavity.

9. A system according to claim 7, wherein the virtual model base comprises a perimeter corresponding to a finish line or demarcation line of the trimmed first model.

10. A system according to claim 7, wherein one of the virtual model base or the virtual model well further comprises at least one virtual projection, and the other one of the virtual model base and the virtual model well further comprises a virtual socket structure for virtually receiving the at least one virtual projection.

11. A system according to claim 10, wherein the at least one virtual projection and virtual socket structure are arranged with respect to the virtual base and virtual well such that the virtual base can be virtually received in the virtual well in only one orientation with respect thereto.

12. A system for manufacturing a physical dental model of a dental site, the system comprising a processor operably coupled to a computer readable storage medium comprising instructions that, when executed, cause the processor to:
    receive a 3D virtual model of the dental site comprising dental surfaces, wherein a first portion of the dental site is obscured by a material;
    trim the 3D virtual model to virtually replace a part of the virtual model comprising the obscured first portion with an auxiliary virtual model comprising a representation of the first portion in which the first portion is not obscured by the material, thereby creating a trimmed 3D virtual model;
    manipulate the trimmed 3D virtual model to create a first virtual model part corresponding to a hard dental surface of the dental site, and a second virtual model part corresponding to a soft dental surface of the dental site; and
    output manufacturing instructions to a manufacturing machine for creating a physical model of the first virtual model part and a physical model of the second virtual model part.

13. A system according to claim 12, wherein the manufacturing instructions include instructions for carrying out a material removal operation on at least one material blank to create the physical models.

14. A system according to claim 12, wherein the material removal operation comprises CNC machining of the at least one material blank.

15. A system according to claim 12, wherein the first virtual model part includes a preparation for a dental coping or a dental prosthesis.

16. A system for manipulating a virtual dental model, the system comprising a processor operably coupled to a computer readable storage medium comprising instructions that, when executed, cause the processor to:
    receive a 3D virtual model of a dental site comprising dental surfaces, wherein a first portion of the dental site is obscured by a material;
    separate the 3D virtual model into a first virtual model part corresponding to an unobscured portion of the dental site and a second virtual model part corresponding to the first portion of the dental site obscured by the material;
    generate an auxiliary 3D virtual model representing an unobscured first portion of the dental site by providing topographical data of the first virtual model part and the second virtual model part so as to reconstruct data of the first portion of the dental site to exclude the material; and
    generate a reconstructed 3D virtual model of the dental site based on the first virtual model part and the auxiliary 3D virtual model.

17. A system according to claim 16, wherein the instructions that, when executed, further cause the processor to output manufacturing instructions to a manufacturing machine for creating a physical model of the reconstructed 3D virtual model of the dental site based on the first virtual model part and the auxiliary 3D virtual model.

18. A system according to claim 17, wherein the manufacturing instructions include instructions for carrying out a material removal operation on at least one material blank to create the physical models.

19. A system according to claim 18, wherein the material removal operation comprises CNC machining of the at least one material blank.

20. A system according to claim 16, wherein the reconstructed 3D virtual model of the dental site includes a preparation for a dental coping or a dental prosthesis.

* * * * *